United States Patent [19]

Pisharodi

[11] Patent Number: 5,697,977
[45] Date of Patent: Dec. 16, 1997

[54] METHOD AND APPARATUS FOR SPONDYLOLISTHESIS REDUCTION

[76] Inventor: Madhavan Pisharodi, 942 Wild Rose La., Brownsville, Tex. 78520

[21] Appl. No.: 482,974

[22] Filed: Jun. 7, 1995

Related U.S. Application Data

[63] Continuation-in-part of PCT/US95/03347, Mar. 17, 1995, which is a continuation-in-part of Ser. No. 210,229, Mar. 18, 1994.

[51] Int. Cl.$^6$ ............................................. A61F 2/44
[52] U.S. Cl. .......................... 623/17; 606/61; 606/63; 606/65
[58] Field of Search ............... 623/16, 17; 606/61, 606/62, 63, 65, 66, 70, 76

[56] References Cited

U.S. PATENT DOCUMENTS

| | | | |
|---|---|---|---|
| 4,696,290 | 9/1987 | Steffee | 606/73 |
| 4,714,469 | 12/1987 | Kenna | 623/17 |
| 5,015,247 | 5/1991 | Michelson | 606/61 |
| 5,059,193 | 10/1991 | Kuslich | 606/61 |
| 5,425,773 | 6/1995 | Boyd et al. | 623/17 |
| 5,431,658 | 7/1995 | Moskovich | 606/99 |
| 5,443,514 | 8/1995 | Steffee | 623/17 |
| 5,454,365 | 10/1995 | Bonutti | 600/204 |

FOREIGN PATENT DOCUMENTS

| | | | |
|---|---|---|---|
| 0042271 | 12/1981 | European Pat. Off. | 623/17 |

*Primary Examiner*—Paul B. Prebilic
*Attorney, Agent, or Firm*—Mark R. Wisner

[57] ABSTRACT

Method and apparatus for reduction of spondylolisthesis involving the insertion of an elongate implant which is split longitudinally into two side-by-side members, one of which is movable relative to the other, into the disk space between two misaligned vertebrae. Each of the members is provided with teeth for engaging the adjacent vertebrae and positioned on the members so as to be located on opposite sides of the implant. The implant formed by the two side-by-side members is generally rectangularly-shaped in cross section, the height of the rectangularly-shaped cross section being less than the width so that the implant can be inserted between the adjacent vertebrae with the lesser, height dimension oriented in the same direction as the axis of the spinal column and the larger width dimension at approximately a right angle to that axis. One of the two members is then moved relative to the other from the first position in which the members are in the abovedescribed, side-by-side relationship along the longitudinal axis of the implant to a second position in which the members are aligned with the respective, adjacent, misaligned vertebrae and the implant is then rotated by approximately 90° to cause the teeth to contact the bodies of the adjacent vertebrae. The two members are then brought back into the first side-by-side relationship to draw the misaligned vertebrae into alignment and the implant is rotated approximately 90° to disengage the teeth from the vertebrae for removal of the implant from the disk space.

11 Claims, 3 Drawing Sheets

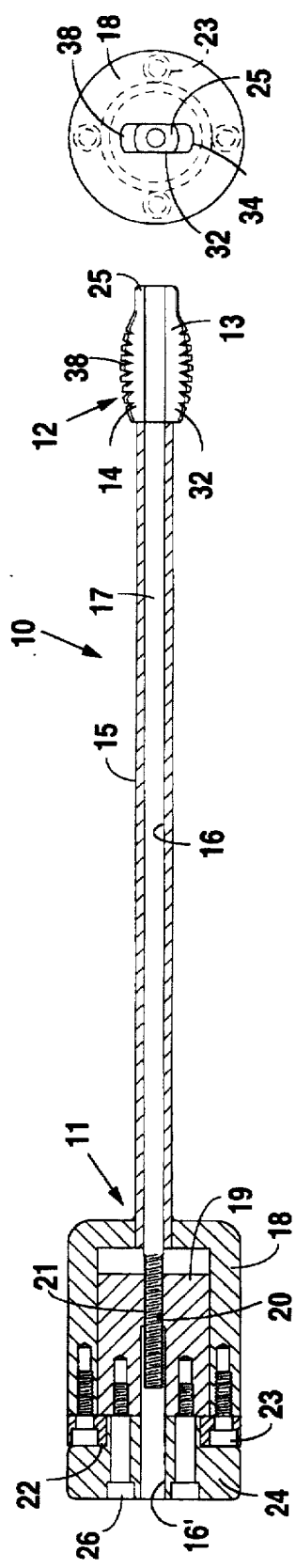
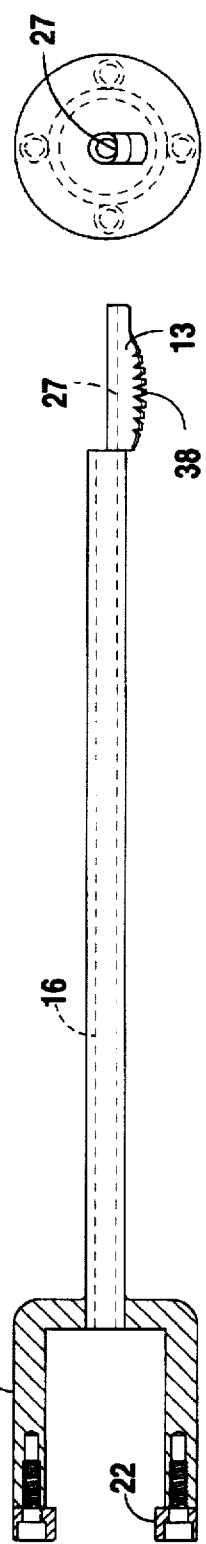
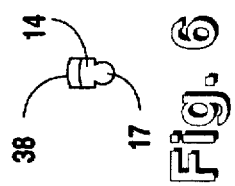
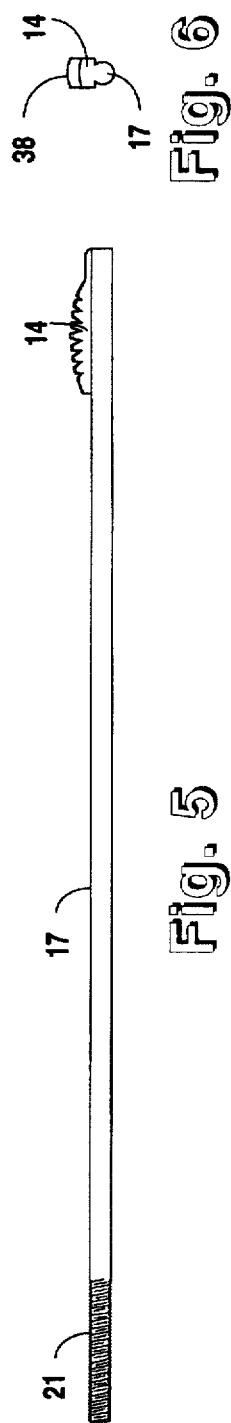
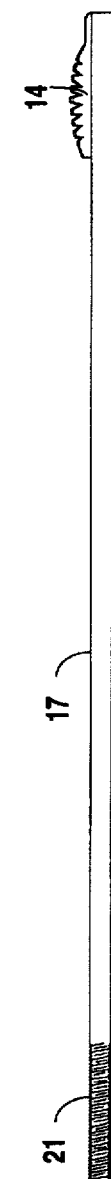

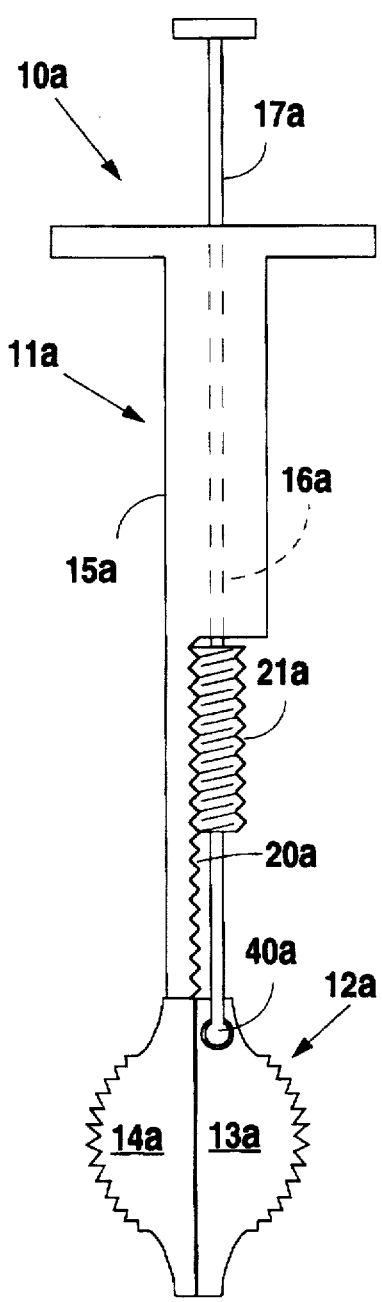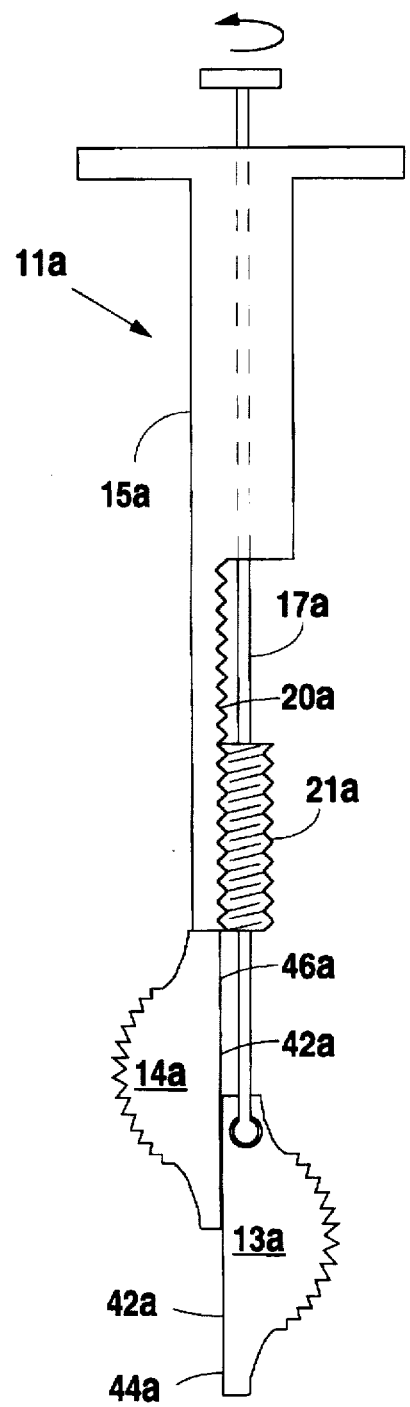

5,697,977

1

METHOD AND APPARATUS FOR SPONDYLOLISTHESIS REDUCTION

CROSS REFERENCE TO RELATED APPLICATION

The present application is a continuation-in-part of the International Application No. PCT/US95/03374, entitled MIDDLE EXPANDED, REMOVABLE, INTERVERTEBRAL DISK IMPLANT AND METHOD OF LUMBAR INTERVERTEBRAL DISK STABILIZATION, filed on Mar. 17, 1995. When filed in the U.S., that National Phase application will itself be a continuation-in-part of U.S. application Ser. No. 08/210,229, filed Mar. 18, 1994 and having that same title.

BACKGROUND OF THE INVENTION

The present invention relates to a method and apparatus for reduction of spondylolisthesis, e.g., misalignment of the vertebrae comprising the spinal column. More specifically, the present invention relates to an apparatus which is inserted into the disk space between two adjacent, misaligned vertebrae, engages the bodies of the adjacent vertebrae, and pulls the adjacent vertebrae back into alignment and a method utilizing that apparatus.

Treatment of disorders of the spinal column, especially in the cervical and lumbar regions, continues to be a challenging field of medicine. Classical treatments for conditions involving subluxation of one vertebrae upon another, resulting in misalignment of the spinal column, involve the use of screws which extend through a plate and which are tightened to draw the misaligned vertebrae back into alignment. However, such conditions often involve damage to the intervertebral disk, e.g., rupture or herniation, which may result in compression of a nerve root. If the herniation is large, compression may be bilateral. This condition is usually not corrected by re-aligning the vertebrae with a plate and screws such that surgical removal of the disk followed by fusion is often indicated after reduction of spondylolisthesis.

However, diskectomy with fusion is not ideal because the replaced bone does not have the function of the cartilaginous tissue of the disk, i.e. no cushioning effect, and has complications because of several factors. First, conventional bone plugs used to pack the disk space do not conform to the space of the disk because the disk bulges maximally in the center. The disk space is wider in the middle and narrower at its anterior and posterior ends. For this reason, the various bone plugs which are currently available commercially have only four contact points, i.e. at the front and back of the disk space. Secondly, access to the disk is from the side of the dorsal spine of the adjacent vertebrae, leaving a space that is "off-center" relative to the bodies of the adjacent vertebrae such that the stability of the implant is even more problematical than might be apparent from the limited contact resulting from the shape of the intervertebral space. Another complication is the possibility of infection or other conditions which may require the removal of the implant. Also, if the bone pieces do not fuse, they may eventually extrude out of the disk space, causing pressure on the nerve roots.

Various prosthetic disk plugs, or implants, are disclosed in the art, but all are characterized by limitations of not conforming to the shape of the disk space, lack of stability when inserted off-center, inability to be removed, or other disadvantages. For instance, U.S. Pat. No. 4,863,476 (and its European counterpart, EP-A-0260044) describes an elongated body divided longitudinally into two portions having

2 a cam device movable therebetween for increasing the space between the two body portions once inserted into the disk space. However, that device is generally cylindrical in shape such that the only contact points between the device and the vertebral bodies are at the front and back of the disk space, creating increased likelihood of instability and generally rendering that device unsuitable for use after partial diskectomy. The art also discloses intervertebral disk prostheses (e.g., U.S. Pat. Nos. 3,867,728, 4,309,777, 4,863,477 and 4,932,969 and French Patent Application No. 8816184) which may have more general contact with the adjacent disks, but which are not intended for use in fusion of the disks. The art also includes spinal joint prostheses such as is described in U.S. Pat. No. 4,759,769, which is again not indicated for use when fusion is the preferred surgical intervention.

There is, therefore, a need for an improved method of treatment of conditions involving misalignment of the vertebrae of the spinal column, or spondylolisthesis, and it is a principal object of the present invention to provide such a method and an apparatus for use in connection with that method.

SUMMARY OF THE INVENTION

This need is met in the present invention by providing an apparatus for aligning vertebrae comprising an elongate handle having a longitudinal bore therethrough, an implant comprised of first and second side-by-side members, the first member being integrally mounted to the handle and the second member being movable relative to the first member in the direction of the longitudinal axis of the handle, and means formed on opposite sides of the implant for selectively engaging adjacent vertebrae to prevent relative movement between the respective first and second members and the adjacent vertebrae. A mandrel is positioned in the bore in the handle and is connected to the second member for moving the second member relative to the first member in the direction of the longitudinal axis of the handle. To facilitate precise movement of the second member relative to the first, and to confer the mechanical advantage on that movement Which may be required to draw the adjacent vertebrae into alignment, the mandrel is preferably threaded and the bore in the handle is provided with a matching set of threads such that rotation of the mandrel causes movement of the second member along the longitudinal axis of the handle.

In a second aspect, the present invention involves a method of aligning adjacent vertebrae after removing a portion of the intervertebral disk from therebetween to form a disk space comprising the steps of inserting an elongate implant having means formed on opposite sides thereof for selectively engaging the vertebrae adjacent the disk space into the disk space, the implant being comprised of first and second side-by-side members, with the vertebrae engaging means extending into the disk space without engaging the adjacent vertebrae and moving the second member relative to the first member until the first and second members are approximately aligned with the adjacent vertebrae. The implant is rotated by approximately 90° to cause the vertebrae engaging means formed thereon to engage the vertebrae and the second member is then moved relative to the first member to align the vertebrae to which it is engaged with the vertebrae to which the first member is engaged. In the preferred embodiment of the method of the present invention, the disk is removed on both sides of the center line of the spine and a second implant, identical to the first, is inserted between the adjacent vertebrae on the side of the disk space opposite the first implant and the misaligned vertebrae are then drawn back into alignment by simultaneous movement of the second members of both implants. One of the two implants is then removed and replaced with a monolithic implant having roughly the same size and shape while the vertebrae are held in alignment by the other implant. After replacement of one implant with a first monolithic implant, the other implant is replaced with a second monolithic implant.

BRIEF DESCRIPTION OF THE DRAWINGS

FIG. 1 is a longitudinal, partial sectional view of a preferred embodiment of the apparatus of the present invention.

FIG. 2 is an end view of the apparatus of FIG. 1.

FIG. 3 is a view similar to that of FIG. 1 but with the mandrel removed therefrom.

FIG. 4 is an end view of the apparatus of FIG. 3.

FIG. 5 is a side, elevational view of the mandrel of the present invention after removal from the apparatus of FIG. 1.

FIG. 6 is an end view of the mandrel of FIG. 5.

FIG. 10 is a top, plan view of an alternative embodiment of the apparatus of the present invention showing the two halves of the body in their first, side-by-side position.

FIG. 11 is a top, plan view of the apparatus of FIG. 10 showing the two halves of the body in the second position.

DETAILED DESCRIPTION OF THE PREFERRED EMBODIMENTS

Figure 7:
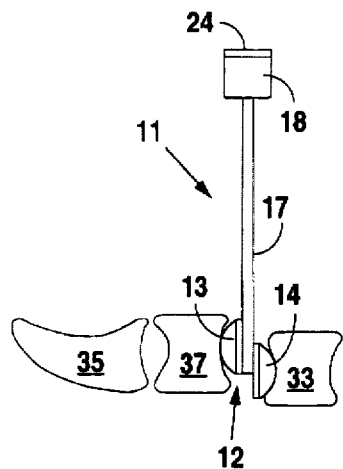
FIG. 7 is a partially schematic, lateral view of a portion of the lumbar spine showing the use of the apparatus of FIG. 1 to align the fourth and fifth lumbar vertebrae.

Referring now to the figures, a presently preferred embodiment of an apparatus for aligning adjacent vertebrae constructed in accordance with the teachings of the present invention is shown in FIG. 1. The apparatus, indicated generally at reference numeral 10 is comprised of an elongate handle 11 and an elongate body 12. The body 12 is comprised of first and second side-by-side members 13 and 14, respectively, the first member 13 being integrally mounted to handle 11 and the second member 14 being movable relative to the first member 13 in the direction of the longitudinal axis of the shaft 15 of handle 11.

The shaft 15 of handle 11 is provided with a longitudinal bore 16 therethrough having a mandrel 17 positioned therein, the second member 14 being mounted to mandrel 17. At the end opposite first member 13, the shaft 15 is provided with a tubular barrel 18 having a collar 19 positioned therein. Collar 19 is also provided with a longitudinal bore 16', the longitudinal axis of which is aligned with the longitudinal axis of the bore 16 in mandrel 17 which is provided with a set of threads 20 for receiving the threaded end 21 of mandrel 17. Collar 19 is retained within barrel 18 by the keeper 22 which is retained on the end of barrel 18 by screws 23. An adjustment knob 24 is integrally mounted to collar 18 by screws 26. As a result of this construction, when mandrel 17 is rotated by turning adjustment knob 24, the second member 14 moves relative to first member 13 from a first position in which the members 13 and 14 are in side-by-side, parallel relationship to each other to a second position along the longitudinal axis of the shaft 15 of handle 11 in which the two members remain parallel to each other but are no longer side-by-side as shown in FIG. 7. Referring to FIGS. 3–6, it can be seen that first member 13 is provided with a half round hollow 27 for receiving the round mandrel 17 for retaining the two members 13 and 14 in tight, parallel, side-by-side relationship when second member 14 is moved from the first position to the second position.

Figure 8:
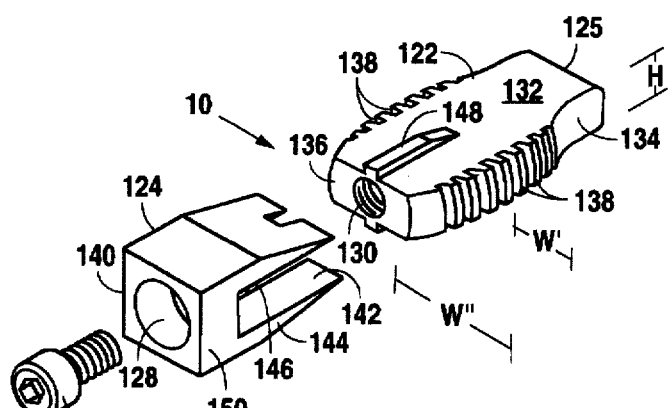
FIG. 8 is an exploded, perspective view of a monolithic implant for use in accordance with the method of the present invention.
Figure 9:
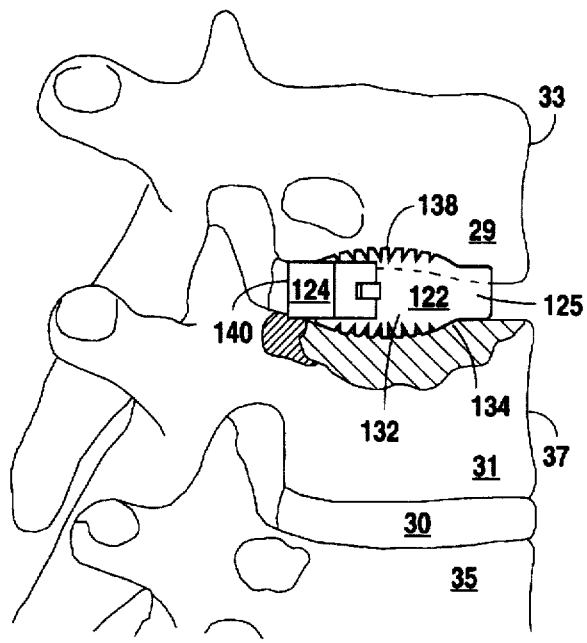
FIG. 9 is a lateral view of the fourth and fifth lumbar vertebrae of a human spinal column having the monolithic implant of FIG. 8 inserted therebetween and having a portion of the bodies of the vertebrae shown cut away and/or in shadow lines to show the engagement of the vertebral bodies by the implant.

When the first and second members 13 and 14 are in the first side-by-side position shown in FIGS. 1 and 2, e.g., when the mandrel 17 is rotated to draw the end 36 of second member 14 against the end 54 of handle 11, the two members 13 and 14 form an elongate body 12 having a shape which is similar to the shape of the monolithic implant 122 shown in FIGS. 8 and 9. Referring, however, to the body 12 for the time being, when side-by-side, the two members 13 and 14 form a body 12 that is comprised of first and second sides 32 and third and fourth sides 34 providing a substantially rectangularly-shaped cross-section. The height H of the rectangularly-shaped cross-section is defined by first and second sides 32 and the width W is defined by the third and fourth sides 34 and, as is apparent by comparison of H and W, the height H of body 12 is less than the width W. As will be explained below, H is minimized to facilitate insertion of the second end 36 into, and positioning of body 12 in, the disk space from which a portion of the intervertebral disk 30 was removed and W is maximized to provide the desired stabilization to adjacent vertebrae 33 and 37. Third and fourth sides 34 are arched from one end of body 12 to the other to provide the portion of body 12 intermediate the ends 25 and 36 with a width W' which is larger than the width W'' at the ends 25 and 36. Because the sides 32 of body 12 are substantially flat and the sides 34 are arched from one end 25 to the other end 36, body 12 is described as being a biplanar, bi-convex body. The convex, or arched, sides 34 of body 12 are provided with a plurality of teeth 38 for biting into the adjacent vertebrae 33 and 37 as will be explained in more detail below. The end 36 of body 12 is formed in a blunt, or rounded shape to reduce the likelihood of injury to the nerves of the spinal cord during insertion into the disk space.

Referring now to FIG. 7, the use of the apparatus 10 for reduction of spondylolisthesis is shown. In FIG. 7, the fourth lumbar vertebrae (L4) 33 is shown as having shifted anteriorally, leaving that vertebrae out of alignment with the fifth lumbar vertebrae (L5) 37 and the first vertebrae comprising the sacrum 35. To correct this misalignment, surgery is performed as in a simple diskectomy and the intervertebral disk (not shown) is exposed through a small laminotomy. Disk material is removed and any nerve root compression is corrected. The posterior longitudinal ligament (not shown) and disk cartilage are removed until the surface of the bodies 29 and 31 of the adjacent vertebrae (L4 and L5) 33 and 37, respectively, are exposed above and below the disk space.

Using spreaders such as those disclosed in International Application No. PCT/US 95/03347, which reference is hereby incorporated into this specification in its entirety by this specific reference thereto, the adjacent vertebrae 33 and 37 are distracted to open the disk space. The body 12 of apparatus 10, having the first and second members 13 and 14 initially in the above-described side-by-side relationship, is then inserted into the disk space with the top and bottom thereof, i.e., the first and second substantially planar sides 32, engaging the adjacent vertebrae 33 and 37 so that the teeth 38 formed on the third and fourth sides 34 of body 12 extend into the disk space without engaging the adjacent vertebrae 33 and 37. The implant is oriented in the disk space so that, when rotated as described below, the first member 13 is the portion of the body 12 which contacts the body 31 of L5 37 and the second member contacts the body 29 of L4 33. In other words, body 12 is oriented so that first member 13 is positioned in close proximity to the body 31 of the vertebrae 37 which is aligned with the axis, or centerline, of the spinal column and second member 14 is positioned in close proximity to the body 29 of the vertebrae 33 which is out of alignment. The body 12 of apparatus 10 is inserted until the middle portion of first member 13 is positioned adjacent the concavity in the upper surface of the body 31 of the L5 37. Using the adjustment knob 24, mandrel 17 is then rotated to advance the second member 14, e.g., the portion having the wider width W'', anteriorally until the middle portion, e.g., the portion having the wider width W'', of second member 14 is positioned adjacent the concavity of the lower surface of the body 29 of L4 33. As noted above, the wider middle portion W'' of each of the members 13 and 14 comprising the body 12 of apparatus 10 provides maximal engagement of the concave shaped surface of the body of the vertebrae when the body 12 is rotated by approximately 90° as described below. Those skilled in the art who have the benefit of this disclosure will recognize that, depending upon the circumstances of each surgery, it may also be advantageous to "pre-adjust" the body 12 by advancing the second member 14 to the second position by the amount of the misalignment before inserting the body 12 of apparatus 10 into the disk space and that the mount of slippage of L4 33 relative to L5 37 is calculated using known methods and/or estimated from X-ray films or other images.

Once the first and second members 13 and 14 are approximately aligned with each of the adjacent vertebrae 33 and 37 by positioning the wide, middle portion of each member in the respective concavities of the vertebrae, using the barrel 18 of handle 11, the body 12 of apparatus 10 is rotated by approximately 90° to cause the teeth 38 formed on the surfaces 34 of first and second members 13 and 14 to engage the bodies 29 and 31 of the respective adjacent vertebrae 33 and 37 as shown in FIG. 7. Using the adjustment knob 24, mandrel 17 is then rotated in the opposite direction to draw second member 14 back into the first, side-by-side, parallel relationship with first member 13, pulling the vertebrae to which it is engaged, i.e., L4 33, back into alignment with L5 37.

For reasons which will be made clear by the following description, in a particularly preferred embodiment of the method of the present invention, the diskectomy and laminotomy are performed bilaterally. In other words, the above-described surgical procedure is performed to the side of the center line of the adjacent vertebrae such that the portion of the intervertebral disk which is removed is "off center" relative to the bodies 29 and 31 of the respective adjacent vertebrae 33 and 37. It is preferred that an identical surgery be performed on the other, or second, side of the center line of the adjacent vertebrae and that the body of a second apparatus (not shown in the figures for purposes of clarity) be inserted into the disk space after that procedure. The adjacent vertebrae 33 and 37 are then aligned by rotation of the respective adjustment knobs 24 of both apparatus 10 until the vertebrae are aligned. In this fashion, the body 12 of one of the two apparatus 10 retains the adjacent vertebrae in alignment even after removal of the other implant.

Removal of the body 12 is accomplished by rotation by approximately 90° (preferably in the direction opposite the direction of rotation which was utilized to cause the teeth 38 to engage the respective adjacent vertebrae 33 and 37) so as to disengage the teeth 38 from L4 33 and L5 37. While the body of the second apparatus remains in the disk space on the second side of the center line, the implant 122 (see FIG. 8) is inserted into the disk space from which the first body 12 was removed. Implant 122 is constructed in essentially the same shape as the body 12 of apparatus 10 when both of the first and second members 13 and 14 are in the first, side-by-side, parallel position described above but is monolithic in its construction, i.e., is not split longitudinally in the manner in which the body 12 of apparatus 10 is split into first and second members 13 and 14. Because of the similarity in the shape and component parts of the body 12 and implant 122, it is not necessary to describe the component parts of monolithic implant 122 in further detail other than to note that the corresponding parts of implant 122 are numbered with the same reference numerals but preceded with a "1", e.g., the teeth 38 of body 12 are numbered as 138 on implant 122. Implant 122 and methods for spinal fusion utilizing implant 122 are described in detail in my co-pending application, filed on the same date as the present application Ser. No. 08/475211, entitled ROTATING, LOCKING, MIDDLE-EXPANDED INTERVERTEBRAL DISK STABILIZER AND METHOD, which is hereby incorporated into this specification in its entirety by this specific reference thereto.

As shown in FIGS. 8 and 9, implant 122 also comprises a lock 124 which is substantially square when viewed from the end 140 along the axis of the bore 128 therethrough and U-shaped when viewed from the side. The inside surfaces 142 of the arms 144 of the U-shaped lock 124 are flat for contacting the first and second sides 132 of monolithic implant 122 to prevent rotation of lock 124 relative to implant 122 when lock 124 is mounted to implant 122 and secured thereto by bolt 126. The surfaces 142 are provided with a slot 146 for receiving a complementary-shaped key 148 (it will be recognized that the key 148 could be formed on the surfaces 142 and that slot 146 could be formed in the first and second sides 132 of implant 122) to facilitate assembly of lock 124 to implant 122 so that the bore 128 in lock 124 is aligned with the bore 130 in implant 122. The sides of the square end 140 of lock 124 provide surfaces 150 for bearing against the bodies 29 and 31 of the respective adjacent vertebrae 33 and 37 as explained below, but it will be recognized by those skilled in the art who have the benefit of this disclosure that the bearing surfaces 150 need not be flat and that the end 140 of lock 124 need not necessarily be square.

The monolithic implant 122 is inserted into the disk space from which the body 12 of the first apparatus 10 is removed on the end of an elongate applicator (not shown here but shown in detail in the above-referenced and incorporated co-pending application) which is provided with threads for mating with the threads in the bore 130 in implant 122. The disk space is then packed with cancellous bone chips (not shown). When the threaded end of the applicator is screwed all the way into the bore 130 so as to prevent relative movement of the implant 122 and its applicator, the monolithic implant 122 is then inserted into the disk space with the flat surfaces 132 adjacent the bodies 29 and 31 of adjacent vertebrae 33 and 37 and moved in an anterior-posterior direction so as to enable the implant 122 to be positioned in the disk space at a position in which the expanded, middle portion and the smaller width ends 125 and 136 of the third and fourth sides 134 of implant 122 contact the respective lower and upper surfaces of the bodies 29 and 31 of the adjacent vertebrae 33 and 37 when rotated by approximately 90° using the applicator. The respective lower and upper surfaces of the bodies 29 and 31 of vertebrae 33 and 37 are slightly concave such that the larger width middle portion W" of implant 122 allows the implant 122 to engage substantially more of the respective surfaces of the vertebral bodies 29 and 31 than conventional prosthetic devices, thereby providing increased stability to the fusion once increased stability to the fusion once further rotation of implant 122 in the disk space is prevented as described below.

Once positioned in the disk space so as to provide maximum stabilization, the applicator is then detached from the monolithic implant 122 by unscrewing and backed out of the incision in the patient. Lock 124 is then inserted through that same incision and, using the slot 146 and key 148, the bore 128 in lock 124 and bore 130 in implant 122 are aligned and the bolt 126 is inserted and tightened to secure lock 124 to the implant 122. Securing the lock 124 to implant 122 in this manner prevents relative rotation between lock 24 and implant 122. Because the bearing surfaces 150 of lock 124 bear against the bodies 29 and 31 of the respective adjacent vertebrae 33 and 37 to prevent rotation of the lock 124 relative to the adjacent vertebrae 33 and 37 against which the bearing surfaces 150 bear, rotation of the implant 122 in the disk space is prevented. Those skilled in the art who have the benefit of this disclosure will recognize that the bearing surfaces 150 bear against the cortical end plate of the bodies 29 and 31 of the respective adjacent vertebrae 33 and 37, which is comprised of non-cancellous bone, and provides a hard, relatively smooth surface against which the bearing surfaces 150 bear. The end 140 of lock 124 is preferably supplied in a plurality of different sizes and shapes other than the square shaped end 140 shown in the figures so as to allow the surgeon to select an appropriately sized and shaped lock which provides a close fit with the space between vertebral bodies. Once the monolithic implant 122 is locked in place on the first side of the center line of the adjacent vertebrae 33 and 37, the body 12 of the second apparatus 10 on the second side of the center line, which has remained in place throughout the procedure, is then removed. The disk space is then packed with cancellous bone chips through this second side and a second monolithic implant (also not shown) is inserted, positioned, rotated, and locked in its place in the same manner as described above.

If necessary, a small amount of a physiologically compatible adhesive of a type known in the art is applied over the cancellous bone chips just medial to the implants to close off the remaining portion of the openings into the disk space. The patient should be able to ambulate soon after the procedure because of the stability imparted to the spinal column by the implant of the present invention. Before narrowing of the disk space occurs, the cancellous bone chips will have started the fusion process.

Referring now to FIGS. 10 and 11, there is shown an alternative embodiment of the apparatus, indicated generally at reference numeral 10a, of the present invention. Where possible, the component parts of apparatus 10a are labelled with the reference numeral (and the "a" designation) of the corresponding parts of the apparatus 10. Apparatus 10a is comprised of a handle 11a and body 12a, the body 12a being comprised of first (fixed) and second (movable) members 13a and 14a, respectively. The second member 14a is mounted to a mandrel 17a positioned in a longitudinal bore 16a in the shaft 15a by a swivel joint 40a and moves relative to first member 13a by action of the threads 21a formed on the outside surface of mandrel 17a on the threads 20a formed on the shaft 15a of handle 11a. The body 12a of apparatus 10a is shaped in the same substantially rectangular cross-sectional shape as the body 12 of apparatus 10 and the component parts of apparatus 10a function in the same manner as the parts of apparatus 10.

Apparatus 10a also includes a plurality of fine serrations 42a formed on the opposed surfaces 44a and 46a of first and second members 13a and 14a, respectively. The serrations 42a act to resist longitudinal movement of second member 14a relative to first member 13a.

Although described in terms of the preferred embodiment shown in the figures, this embodiment is shown to exemplify the present invention, it being recognized by those skilled in the art that certain changes can be made to the specific structure of the preferred embodiment shown and described without departing from the spirit of the present invention. All such modifications are intended to fall within the scope of the following claims.

What is claimed is:

1. A method of aligning adjacent vertebrae after removing a portion of the intervertebral disk from therebetween to form a disk space comprising the steps of:
    inserting an elongate body having means formed on opposite sides thereof for selectively engaging the vertebrae adjacent the disk space into the disk space, the body being comprised of first and second side-by-side members, with the vertebrae engaging means extending into the disk space without engaging the adjacent vertebrae;
    moving the second member relative to the first member until the first and second members are approximately aligned with each of the adjacent vertebrae;
    rotating the body approximately 90° to cause the vertebrae engaging means thereon to engage the vertebrae; and
    moving the second member relative to the first member to align the vertebrae to which each member is engaged.

2. The method of claim 1 wherein the first and second members are moved by moving a mandrel to which the second member is mounted.

3. The method of claim 1 wherein the body is elongate and wider in the middle portion than at the ends thereof and the first and second members are aligned with the adjacent vertebrae by positioning at the point relative to the adjacent vertebrae at which the respective wider middle portions maximally engage the respective adjacent vertebrae.

4. The method of claim 1 wherein the body is substantially rectangularly-shaped in cross section, the sides of the body defining a height of smaller dimension than the dimension of the sides defining the width of the body, the vertebrae engaging means being formed on the sides of the body defining the height thereof.

5. The method of claim 1 wherein the body is inserted into the disk space on one side of the center of the adjacent vertebrae.

6. The method of claim 1 additionally comprising replacing the first body with a monolithic implant after aligning the adjacent vertebrae.

7. The method of claim 6 additionally comprising replacing the second body with a second monolithic implant.

8. A method of aligning adjacent vertebrae after removing portions of the intervertebral disk from therebetween to form first and second disk spaces on the sides of the center thereof comprising the steps of:

inserting a first elongate body having means formed thereon for selectively engaging the vertebrae adjacent the disk space into the first disk space, the first body being comprised of first and second side-by-side members;

moving the second member of the first body relative to the first member of the first body to a position in which the first and second members of the first body are approximately aligned with the adjacent vertebrae;

rotating the first body approximately 90° to cause the vertebrae engaging means formed thereon to engage the adjacent vertebrae;

moving the second member of the first body relative to the first member of the first body to align the adjacent vertebrae;

inserting a second elongate body having means formed thereon for selectively engaging the adjacent vertebrae into the second disk space, the second implant being comprised of first and second side-by-side members;

moving the second member of the second body relative to the first member of the second body to a position in which the first and second members of the second body are approximately aligned with the adjacent vertebrae;

rotating the second body approximately 90° to cause the vertebrae engaging means formed thereon to engage the adjacent vertebrae; and moving the second member of the second body relative to the first member of the second body to align the adjacent vertebrae.

9. The method of claim 8 wherein the first and second members of the first and second bodies are moved by moving a mandrel to which the respective second members are mounted.

10. The method of claim 8 wherein the first and second elongate bodies are wider in the respective middle portions than at the ends thereof.

11. The method of claim 8 wherein the first and second elongate bodies are substantially rectangularly-shaped in cross section, the sides of the respective bodies defining the height being of smaller dimension than the dimension of the sides defining the width of the respective bodies, and the vertebrae engaging means are formed on the sides of the respective bodies defining the height thereof.

* * * * *